United States Patent [19]

Quarderer et al.

[11] Patent Number: 4,749,724

[45] Date of Patent: Jun. 7, 1988

[54] PROCESS FOR PRODUCING ALCOHOLS FROM SYNTHESIS GAS

[75] Inventors: George J. Quarderer; Gene A. Cochran, both of Midland, Mich.

[73] Assignee: The Dow Chemical Company, Midland, Mich.

[21] Appl. No.: 933,409

[22] Filed: Nov. 20, 1986

Related U.S. Application Data

[63] Continuation of Ser. No. 622,029, Jun. 18, 1984, abandoned, which is a continuation-in-part of Ser. No. 476,674, Mar. 18, 1983, abandoned.

[51] Int. Cl.⁴ .............................................. C07C 27/06
[52] U.S. Cl. ...................................... 518/714; 518/713
[58] Field of Search ................................. 518/714, 713

[56] References Cited

U.S. PATENT DOCUMENTS

| | | |
|---|---|---|
| 1,859,244 | 5/1932 | Patort . |
| 2,490,488 | 12/1949 | Stewart . |
| 3,972,952 | 8/1976 | Clark . |
| 4,151,190 | 4/1979 | Murchison et al. . |
| 4,210,597 | 7/1980 | Huang . |
| 4,261,864 | 4/1981 | Nargis . |
| 4,380,589 | 4/1983 | Murchison et al. . |
| 4,607,055 | 8/1986 | Grazioso et al. . |
| 4,607,056 | 8/1986 | Grazioso et al. . |
| 4,616,040 | 10/1986 | Grazioso et al. . |
| 4,661,525 | 4/1987 | Grazioso et al. . |

FOREIGN PATENT DOCUMENTS

| | | |
|---|---|---|
| 5492 | 11/1979 | European Pat. Off. . |
| 0100607 | 7/1983 | European Pat. Off. . |
| 1058797 | 11/1953 | France . |
| 238319 | 8/1925 | United Kingdom . |
| 2076015 | 11/1981 | United Kingdom . |

OTHER PUBLICATIONS

Anderson et al. I.& E.C. vol. 44, No. 10, pp. 2418–2424, 1952.

British Coal Corporation Letter dated Jul. 6, 1987 from I. C. Wishart, Authorized Representative No. 3426.

*Primary Examiner*—Howard T. Mars
*Attorney, Agent, or Firm*—Charles J. Enright

[57] ABSTRACT

A Fischer-Tropsch reaction to form alcohols from hydrogen and carbon monoxide, using a catalyst containing:

(1) at least one element selected from the group consisting of molybdenum, tungsten and rhenium in free or combined form;

(2) a promoter comprising an alkali or alkaline earth element in free or combined form; and optionally (3) a support;

forms an alcohol fraction boiling in the range of motor gasoline in at least about 20 percent $CO_2$ free carbon selectivity.

41 Claims, No Drawings

PROCESS FOR PRODUCING ALCOHOLS FROM SYNTHESIS GAS

CROSS REFERENCE TO RELATED APPLICATION

This is a continuation of application Ser. No. 622,029 filed June 18, 1984, now abandoned which is a continuation-in-part of U.S. Ser. No. 476,674 filed Mar. 18, 1983 now abandoned.

FIELD OF THE INVENTION

This invention relates to a Fischer-Tropsch process for making alcohols and describes the catalyst composition and conditions of the process.

BACKGROUND OF THE INVENTION

Almost as old as the Fischer-Tropsch process for making hydrocarbons is the Fischer-Tropsch process for making alcohols. The reaction is carried out by passing a mixture of carbon monoxide and hydrogen over a catalyst for the hydrogenation of the carbon monoxide. A typical review article is R. B. Anderson et al., *Industrial and Engineering Chemistry*, Vol. 44, No. 10, pp. 2418-2424. This paper lists a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favoring the production of alcohols are high pressure, low temperature, high space velocity, high recycle ratio and carbon monoxide-rich synthesis gas.

Molybdenum is known to be catalytic for the Fischer-Tropsch process and is taught in U.S. Pat. Nos. 4,151,190 and 4,199,522 which are incorporated herein by reference. The references describe some of the herein used catalysts but do not teach that the catalysts are useful for making commercially significant quantities of alcohols.

U.S. Pat. No. 2,490,488 discloses that molybdenum sulfide methanation catalysts acquire Fischer-Tropsch activity when promoted with an alkaline compound of an alkali metal. The example of the invention shows a 30% selectivity to $C_3+$ hydrocarbons and oxygenates. Of this 30%, no more than 44% boils near or above 65° C. the boiling point of methanol. Accordingly the maximum possible alcohol selectivity is no more than 13.2% (44% of 30%).

U.S. Pat. No. 2,539,414 describes a Fischer-Tropsch process with molybdenum carbide catalysts. It teaches that the catalyst may be used to form oxygenates and at column 3, lines 66-71 teaches that one might get alcohols or hydrocarbons by varying the conditions.

G. T. Morgan et al., *J. Soc. Chem. Ind.*, Vol. 51, 1932 Jan. 8, pp. 1T-7T, describe a process for making alcohols with chromium/manganese oxide catalysts promoted with alkali.

A number of references teach production of alcohols using rhodium catalysts. Some of these contain molybdenum as an optional ingredient. U.S. Pat. No. 4,014,913 discloses a catalyst containing rhodium and thorium or uranium and iron or molybdenum or tungsten for the production of ethanol. U.S. Pat. No. 4,096,164 discloses the use of rhodium in combination with molybdenum or tungsten and Example A discloses that use of a molybdenum-on-silica catalyst yielded 4.4 percent oxygenates.

EPO application No. 81-33,212 (Chemical Abstracts 96: 51,800a) discloses a similar process using rhodium in combination with one or more of a long list of metals which includes molybdenum.

EPO application No. 79-5,492 (Chemical Abstracts 92: 166,257b), Hardman et al., discloses the production of alcohols using a 4-component catalyst. The first component is copper, the second is thorium, the third an alkali metal promoter and the fourth a long list of metals one of which is molybdenum. Chemical Abstracts 96: 106,913x, Diffenbach et al., disclose a nitrided iron catalyst which is promoted with molybdenum for making alcohols from synthesis gas.

All of the aforementioned references are hereby incorporated by reference.

To make a commercially significant alcohol process, one must use a catalyst and conditions which are highly efficient. To be efficient the catalyst must yield a high ratio of mass of product per given mass of catalyst in a given period of time. The catalyst must be stable and active for long periods of time between regenerations. This may be particularly difficult to accomplish when the $H_2/CO$ ratio of the feed gas is low, such as less than 2 to 1. Ideally the catalyst will have a high selectivity to a commercial product to avoid purification or removal and disposal of by-products and to avoid separation into two or more product streams.

OBJECTS OF THE INVENTION

It is an object of this invention to prepare alcohols in a Fischer-Tropsch type reaction from $H_2/CO$ synthesis gas. It is a preferred object of this invention to make a high yield of alcohols with a catalyst which is selective to alcohols boiling in the range of motor gasoline and that is stable, particularly at low $H_2/CO$ ratios, and active over long periods of time.

SUMMARY OF THE INVENTION

One or more of these objects of the invention are effected by a process for making alcohols comprising contacting a mixture of hydrogen and carbon monoxide with a catalyst comprising:

(1) at least one element selected from the group consisting of molybdenum, tungsten and rhenium in free or combined form;

(2) a promoter comprising an alkali or alkaline earth element in free or combined form; and optionally (3) a support;

to form an alcohol fraction boiling in the range of motor gasoline in at least 20 percent $CO_2$ free carbon selectivity.

It is a feature of this invention, that high yields and selectivity may be obtained without the use of rhodium, copper, ruthenium, zinc or iron. An advantage of the invention is that high production rates may be obtained at high selectivities. Under preferred conditions, these catalysts may yield high $C_1$-$C_4$ alcohol productivity. Up to about 0.3 weight units $C_1$-$C_4$ alcohol/hr/weight unit of catalyst may be achieved. Because of the high selectivity, complex purification steps may be avoided and the alcohol product may have a low acid content and have a high octane blending value. This may permit direct blending into motor fuels without elaborate processing.

DETAILED DESCRIPTION OF THE INVENTION

The hydrogen and carbon monoxide required for this process can be obtained by methods known in the art. Examples are gasification of hydrocarbonaceous materials such as coal, high specific gravity oils, or natural gas; as a by-product of partial combustion cracking of hydrocarbons; by steam reforming of liquid or gaseous hydrocarbons; through the water gas shift reaction; or some combination of these. The two components may also be generated separately and combined for the subject reaction. The molar ratio of hydrogen to carbon monoxide in the feed gas which contacts the catalyst ranges generally from about 0.25 to about 100, preferably from about 0.5 to about 5 and more preferably from about 0.7 to about 3. A most preferred range is from about 0.7 to about 1.5.

Impurities in the feed gas may or may not have an effect on the reaction, depending on their nature and concentration. Carbon dioxide is preferably present at a partial pressure of less than one atmosphere (0.1 MPa) and at that pressure has little deleterious effect. If reactor effluent gas is recycled to the feed, oxygenates, water, and carbon dioxide are preferably removed. Hydrocarbons are most preferably also removed from the recycle stream prior to reintroduction into the reactor.

Generally, the selectivity to alcohols is dependent on the pressure. In the normal operating ranges, the higher the pressure at a given temperature, the more selective the process will be to alcohols. The minimum contemplated pressure is about 500 psig (3.55 MPa). The preferred minimum is about 750 psig (5.27 MPa) with about 1,000 psig (7.00 MPa) being a more preferred minimum. While about 1,500 psig (10.4 MPa) to about 4,000 psig (27.7 MPa) is the most desirable range, higher pressures may be used and are limited primarily by cost of the high pressure vessels and compressors needed to carry out the higher pressure reactions. A typical maximum is about 10,000 psig (69.1 MPa) with about 5,000 psig (34.6 MPa) a more preferred maximum. A most preferred operating pressure is about 3,000 psig (20.8 MPa).

The selectivity to alcohols is also a function of temperature and is interrelated with the pressure function. The minimum temperature used is governed by productivity considerations and the fact that at temperatures below about 200° C. volatile catalytic metal carbonyls may form. Accordingly, the minimum temperature is generally around 200° C.

At a constant pressure, as the temperature increases, the selectivity to alcohols decreases. In other words, at lower pressures one is limited to lower maximum temperatures in order to obtain a given selectivity. For example, at 500 psig (3.55 MPa), the maximum temperature to obtain a net selectivity to alcohols of greater than 20 percent is about 325° C. At 1,000 psig (7.00 MPa), a net selectivity of 20 percent or more may be achieved at a temperature of about 350° C. or less. At a pressure of 1,500 psig (10.4 MPa), a net selectivity to alcohols of 20 percent or greater may be obtained at about 375° C. or less. At higher pressures, one may obtain 20 percent selectivity at up to about 400° C. However, the preferred range of operation is from about 240° C. to about 325° C.

The $H_2$/CO gas hourly space velocity (GHSV) is a measure of the volume of hydrogen plus carbon monoxide gas at standard temperature and pressure passing a given volume of catalyst in an hour's time. This may range from about 100 to about 10,000 hour$^{-1}$ and preferably from about 300 to about 5,000 hour$^{-1}$. Selectivity to the alcohols generally increases as the space velocity increases. However, conversion of carbon monoxide decreases as space velocity increases.

Preferably at least a portion of the unconverted hydrogen and carbon monoxide in the effluent gas from the reaction, more preferably after removal of product alcohols, water and carbon dioxide formed and even more preferably any hydrocarbons formed, may be recycled to the reaction. The amount of recycle is expressed as the recycle ratio which is the ratio of moles of gases in the recycle stream to the moles of gases in the fresh feed stream. A recycle ratio of zero is within the scope of the invention with at least some recycle preferred. A recycle ratio of at least about one is more preferred and at least about three is most preferred.

In addition, the synthesis should be carried out at as little feed conversion per pass as is compatible with economic constraints related to the separation of the alcohol products from unreacted feed and hydrocarbon gases. Accordingly one would increase the space velocity and recycle ratios to preferably obtain about 15–25% conversion per pass.

With preferred catalysts and under preferred conditions of temperatures, pressures, $H_2$/CO ratio, GHSV and recycle ratio, about 0.1 grams of alcohols or more per hour may be formed per gram of catalyst. Under the more preferred conditions of about 300° C., 1500 psig (10.4 MPa), 5,000 hour$^{-1}$ and a $H_2$/CO ratio of about 1.25:1, with a Mo/K on carbon catalyst, about 0.3 grams of alcohol or more per hour per gram of catalyst may be obtained. Under the most preferred conditions of about 280° C., 3,000 psig (20.7 MPa), a GHSV of 5,000 and a $H_2$/CO ratio of 1.2; with a bulk $MoS_2$ catalyst about 0.6 grams of alcohols or more per hour per gram of catalyst may be obtained.

Under the most preferred conditions, alcohols may be obtained in about an 85 percent $CO_2$ free carbon selectivity. The $CO_2$ free carbon selectivity is defined as 100 times the moles of carbon present in a product fraction divided by the total moles of carbon in all products which are not $CO_2$ or unconverted feed. For example, if one mole of ethanol is found in the alcohol fraction, this is counted as 2 moles of carbon. Carbon dioxide and water are not counted as products in this calculation.

The first component of the catalyst preferably consists essentially of at least one member selected from the group consisting of molybdenum, tungsten and rhenium in free or combined form. Molybdenum and tungsten are preferred and molybdenum is most preferred.

The molybdenum, tungsten or rhenium may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetyl acetonates, oxalates, etc., carbonyls, and the like. Representative compounds also include the elements in anionic form such as molybdates, phosphomolybdates, tungstates, phosphotungstates, and the like, and include the alkali, alkaline earth, rare earth and actinide series salts of these anions. The sulfides, carbonyls, carbides and oxides are preferred with the sulfide being most preferred.

The molybdenum, tungsten or rhenium may be present in an amount based on the weight of the total catalyst of at least about two percent, preferably at least about 5 percent with an upper limit of about 70 percent and preferably about 30 percent of the total catalyst when the catalyst is supported.

When unsupported molybdenum, tungsten or rhenium is present, it is present in about stoichiometric quantities in relation to other elements with which it may be combined as a compound. Other materials would also have to be considered with respect to fraction of catalyst that is the active metal, such as, agglomerating agents, binders, pelleting lubricants, promoters and possible other catalytic materials.

The promoter may consist essentially of one or more alkali elements or alkaline earth elements in free or combined form. Alkali elements include lithium, sodium, potassium, rubidium and cesium. Alkaline earth elements include: beryllium, magnesium, calcium, strontium and barium. Alkali elements and in particular, cesium and potassium, are preferred. Potassium is most preferred.

The promoter may be present in free or combined form as a metal, oxide, hydroxide, sulfide or as a salt or a combination of these. The alkaline promoter is preferably present at a level sufficient to render the support or the bulk catalyst netural or basic. The promoter is generally present in an amount of at least about 0.05 weight percent as a free element in the finished catalyst. Preferably it is present in an amount of at least about 0.1 percent and most preferably at least 0.5 percent. Large amounts up to about 20 percent of the promoter may be present. Preferably the promoter is present at less than 10 percent.

The promoter may be added as an ingredient to the molybdenum, tungsten or rhenium component or to the support or may be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

A third optional component of the catalyst is a support which may assume any physical form such as pellets, granules, beads, extrudates, etc. The supports may be coprecipitated with the active metal species, or the support in powder form may be treated with the active metal species and then used as is or formed into the aforementioned shapes, or the support may be formed into the aforementioned shapes and then treated with the active catalytic species.

The catalytic species may be dispersed on the support by methods known in the art. Examples include: impregnation from solution, vapor deposition, intimate physical mixing and the like. One or more of these methods may be used. One method of depositing the catalytic species on a support is a combination of an incipient wetness technique and physical mixing with decomposition of a carbonyl. A preferred method is the in situ precipitation of a molybdenum, tungsten or rhenium sulfide on the support.

A first step in the first method of placing the catalyst and/or promoters on the support is known as the incipient wetness technique. Water- or solvent-soluble salts of the metals to be dispersed on the support are chosen. The soluble salts which may be a single salt or more than one salt are dissolved in a quantity of solvent which may be aqueous, nonaqueous or a mixed solvent. A sufficient quantity of the resulting solution is added to the support in an amount no more than will be completely absorbed by the support. The solvent is then evaporated to leave the salt dispersed on the support. Depending on the solubility of the salt chosen and on the quantity of the element desired to be dispersed on the support, this process may be performed once or several times. Impregnations with two or more species may be performed by codissolving them into the solvent or by adding them separately in different quantities or types of solvent. In addition to evaporating the solvent, the loaded support may be heated in air, hydrogen, nitrogen or other atmosphere to obtain the catalytic species in their final form. Reduction in hydrogen at mildly elevated pressures at from about 250° C. to about 500° C. is preferred for these supported catalysts. The wetting, evaporating and heating steps may be repeated several times in order to achieve the desired concentration of catalytic species or promoter on the support. The catalyst may be used at this point or the following additional step may be employed.

In the second step of the first method, a carbonyl of the metal to be dispersed is dry mixed with the resultant metal on a support from the incipient wetness impregnation step. This metal may be the same or different from the first metal. After intimate mixing, the mixture is calcined in flowing nitrogen to drive off CO and yield the catalyst ready for use. This second step may also be employed as the sole step for loading the metal on the support or in combination with other steps.

The preferred supported catalyst is made by impregnating the support with a soluble salt of molybdenum, tungsten or rhenium that may be decomposed to the sulfide. For example, a solution of $(NH_4)_2MoS_4$ with or without a promoter such as $K_2CO_3$ may be impregnated onto a support. The $(NH_4)_2MoS_4$ may then be decomposed by heat to $MoS_2$. $(NH_4)MoS_4$ may be prepared by mixing a solution of $(NH_4)_4Mo_7O_{24}$ with ammonium hydroxide and aqueous ammonium sulfide solution.

Exemplary support materials include: the aluminas, basic oxides, the silicas, carbons, or suitable solid compounds of magnesium calcium, strontium, barium, scandium, yttrium, lanthanum and the rare earths, titanium, zirconium, hafnium, vanadium, niobium, tantalum, thorium, uranium, and zinc. Oxides are exemplary suitable solid compounds. Preferably the supports are neutral or basic or may be rendered neutral or basic by addition of the alkaline promoters. The aluminas include the alpha, gamma, and eta types. The silicas include for example, silica gel, diatomaceous earth, and crystalline silicates.

The carbons supports, which are preferred supports, include activated carbons such as those prepared from coals and coal-like materials, petroleum-derived carbons and animal- and vegetable-derived carbons. Preferably the carbon support will have a surface area of 1-1500 m²/g, more preferably 10-1000 m²/g and most preferably 100-500 m²/g as measured by the BET nitrogen test. Preferably, micropores (<20 Å (<2 nm)) are minimized and at least twenty percent of the volume of the pores comprises pores having a diameter of from about 20 Å to about 600 Å. Examples include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total catalyst, the support when present generally comprises at least about 20 percent of the catalyst and generally not more than about 98 percent of the catalyst. Preferably the support comprises at least about 50 weight percent and most preferably at least about 70 weight percent of the catalyst.

For several reasons the preferred form of the catalyst is the agglomerated sulfide. Certain forms of molybdenum sulfide are most preferred.

Methods for making molybdenum, tungsten or rhenium sulfides are disclosed generally at pages 23–34 of *Sulphide Catalysts Their Properties and Applications*, O. Weisser and S. Landa, Pergamon Press, New York, 1973 the whole of which is incorporated herein by reference.

Molybdenum sulfide catalysts may be made by thermal decomposition of ammonium tetrathiomolybdate or other thiomolybdates as disclosed in U.S. Pat. Nos. 4,243,553 and 4,243,554 which are hereby incorporated by reference, from purchased active molybdenum sulfides, or by calcining $MoS_3$. Preferred is the decomposition of ammonium tetrathiomolybdate that is formed by precipitation from a solution of ammonium heptamolybdate with ammonium sulfide followed by spray drying and calcining to form the molybdenum sulfide. The molybdenum sulfide may also be precipitated directly on to a support, but the unsupported molybdenum sulfide is preferred. Tungsten or rhenium sulfides may be similarly made. An unsupported catalyst preferably has a surface area of at least 10 $m^2/g$ and more preferably more than 20 $m^2/g$ as measured by the BET nitrogen surface area test.

The alkali or alkaline earth promoter may be added to the active catalytic element prior to, during or after the formation of the sulfide by physical mixing or solution impregnation. The active metal sulfide may then be combined with binders such as bentonite clay, and/or pelleting lubricants such as Sterotex ® and formed into shapes for use as a catalyst.

The finished catalyst may be used in a fixed bed, moving bed, fluid bed, ebullated bed or a graded bed wherein concentration and/or activity of the catalyst varies from inlet to outlet in similar manner to known catalysts. The catalyst may be used in powdered form or may be formed into shapes with or without a binder.

The catalysts of the invention may be employed individually or in combination with other inventive catalysts or with other previously proposed catalysts and activators for the claimed process. In general, the presently taught catalysts when used per se, embody numerous advantages including those mentioned above. On the other hand, in combination with conventional catalysts, they may tend, progressively, to modify the usual effects in accordance with their individual characteristics so that quantitatively intermediate results may be achieved. In short, the catalysts of the present invention may be combined, for example, with typical hydrogenation catalysts such as cobalt and nickel, and with dehydration catalysts such as aluminas and zeolites to effect desired additional results.

However, the catalysts of the invention preferably contain less than 25 weight percent, based on the total weight of carbon oxide hydrogenation active metals, or other carbon oxide hydrogenation active metals and more preferably less than 20 weight percent and most preferably less than 2 weight percent. The catalyst may also be essentially free of other carbon oxide hydrogenating components. By essentially free it is meant that other carbon oxide hydrogenating components do not significantly alter the character or quantity of the alcohol fraction. For example, a significant change would be a five percent change in the amount of the alcohol fraction or a five percent change in the percentage of any alcohol in the alcohol fraction.

Carbon oxide hydrogenating components present in thus limited quantities or excluded are preferably those that contain chromium, manganese, iron, cobalt, copper, zinc, ruthenium and rhodium. More preferably, in addition to the above-mentioned components, those that contain: halogen, titanium, vanadium, cerium, thorium, uranium, iridium, palladium, platinum, silver and cadmium are excluded. Most preferably, components containing chromium, manganese group IIIB elements, including the lanthanides and actinides, groups IVB, VB, VIII, IB and IIB elements are excluded.

Under preferred conditions the catalyst is stable for long periods of time and under ideal conditions may be stable and active for as many as 2000 hours or more. Activity and selectivity are preferably substantially retained after 100 hours of operation, more preferably after 500 hours and most preferably after 1000 hours operation. In the case of reduced oxide catalysts, declines in activity and selectivity may generally be regenerated by reduction with hydrogen after which the catalyst may regain most of its original activity and be used for another long period of time before regenerating again.

At the conditions described above, the process yields substantial quantities of alcohols. Under preferred conditions, the weight units per hour of alcohols boiling in the range of motor gasoline per weight unit of catalyst may exceed 0.2. Under ideal conditions, it may exceed 0.4 and even 0.6.

Of the alcohols formed with supported reduced $MoO_3$ catalysts such as that in Examples 1, 2 and 5, the largest single component is methanol which is typically above about 20 weight percent of the alcohol fraction and generally above about 40 weight percent but generally less than about 70 weight percent and preferably less than about 60 weight percent of the alcohols formed. The next most abundant component may be ethanol which is typically greater than about 15 weight percent of the alcohol fraction and often approaches or exceeds about 30 weight percent. The $C_5+$ alcohols are generally about 10 weight percent or less of the alcohol fraction.

With $MoS_2$ catalysts one may decrease the percentage of methanol in the mixed alcohols fraction by increasing the addition rate of a sulfur releasing substance to the $H_2/CO$ feed. Decreasing the sulfur releasing substance addition rate increases the percentage of methanol in the alcohol fraction. Hydrogen sulfide is a suitable sulfur releasing substance.

The alcohol fraction formed at greater than a 20 percent $CO_2$ free carbon selectivity boils in the motor gasoline range. The minimum boiling pure alcohol is methanol at 64.7° C. ASTM D-439 calls for a 225° C. endpoint for automotive gasoline. Accordingly the alcohol fraction formed at greater than a 20 percent $CO_2$ free carbon selectivity may boil in the range of from about 60° C. to about 225° C. when distilled by ASTM D-86. Other alcohols may boil outside this range but preferably do not. It is not necessary that the entire liquid product boil in this range, but it is preferred. It is not necessary that the alcohol fraction meet all the distillation specifications for motor gasolines; only that it boil within the broad range of motor gasolines. For example, it need not be within 50 percent evaporated limits as set by ASTM D-439. Only 20 carbon mole percent of the total $CO_2$ free product must be alcohols that boil in this range.

The alcohol fraction formed may be used as a motor fuel blending stock. Preferably, the alcohol fraction formed will have a research octane blending value in motor gasoline of greater than about 100, more preferably greater than about 110 and most preferably greater than about 120.

Preferably, a $C_1$–$C_8$ alcohol fraction is formed in at least about 20 percent $CO_2$ free carbon selectivity and most preferably a $C_1$–$C_4$ alcohol fraction is formed in at least about 20 percent $CO_2$ free carbon selectivity.

The $C_1$–$C_4$ alcohol fraction may contain methanol, ethanol, 2-propanol, 1-propanol, 1-butanol, 2-butanol, and 2-methyl-1-propanol, but doesn't generally contain substantial 2-methyl-2-propanol. In addition to these named alcohols the $C_1$–$C_8$ alcohol fraction may contain the $C_5$–$C_8$ alcohols wherein the hydroxyl group may be attached to a carbon which is attached to one or two other carbon atoms.

Under preferred conditions, the amount of water formed is substantially less than the amount of alcohols formed. Typically there is less than 20 weight percent and preferably less than 10 weight percent water based on the quantity of alcohol. This water may be removed by known techniques if the alcohol fraction is to be used as a motor fuel additive. If the water content is about 5 weight percent or less based on alcohols, the water may advantageously be removed by absorption on molecular sieves. At higher water contents one may use a water gas shift drying step as disclosed in British Patent Publication Nos. 2,076,015 and 2,076,423; U.S. patent application No. 508,625, filed June 28, 1983. These references are hereby incorporated herein by reference.

The product mixture, as formed under preferred conditions, contains only small portions of other oxygenated compounds besides alcohols. These other compounds may not be deleterious to using the product, as is, in motor fuels.

In all cases, the alcohol fraction is formed in at least about 20 percent $CO_2$ free carbon selectivity. Preferably the alcohol fraction is formed in at least about 30 percent $CO_2$ free carbon selectivity, more preferably greater than about 50 percent and ideally can be greater than about 70 percent.

Preferably the co-products formed with the alcohol fraction are primarily gaseous products. That is $C_1$–$C_4$ hydrocarbons. Preferably $C_5+$ hydrocarbons are co-produced at less than about 20 percent $CO_2$ free carbon selectivity, more preferably at less than 10 percent and most preferably at less than 5 percent. Lower amounts of normally liquid hydrocarbons make the normally liquid alcohols easier to separate from by-products.

Generally, alcohol selectivity may be increased by increasing pressure, space velocity, product gas recycle ratio and by decreasing $H_2/CO$ feed ratio and temperature.

EXAMPLES

Catalyst Supports

Examples 1, 2 and 5 incorporate supports of Calgon ® Type BPL III Granular Carbon. This is made from selected grades of bituminous coal combined with suitable binders. The mean particle size by weight calculated from the sieve analysis is 113μ. The bulk density is 0.55 g/cm³. The specific surface area evaluated from the three-parameter BET equation using nitrogen adsorption is 1159 m²/g. Total pore volume was measured by the nitrogen uptake at saturation. The mean pore diameter, calculated from the equation $$D = 4 \times \frac{\text{(Total pore volume)}}{\text{(specific surface area)}} \times 10^4$$

is 28 Å (2.8 nm), assuming that the total pore volume is contained in a cylindrical pore having surface area $S_{BET}$. Thirty-three (33) percent of the pores are mesopores as calculated from, percent mesoporosity equals $$\frac{\text{(cumulative volume of pores in 20–600 Å (2.0–60 nm) range)}}{\text{(total volume of pores)}} \times 100.$$

Example 4 incorporates a group of supports including Union Carbide ® MBV, MBT, SBV, TS-1564 and TS-1567 carbons, which are now available from Witco Chemical Corporation. The MBV and MBT carbons are coal based. The SBV carbon is coconut shell-based. The averages of the supports' properties are: particle size—3/16-inch (4.8 mm) extrudates; bulk density—0.67 g/cm³; specific surface area—1179 m²/g; mean pore diameter—18 Å (1.8 nm); and 27 percent mesoporosity.

Catalyst Preparation

The catalyst for Examples 3, 6, 7 and 8 is SN-5613, purchased as is from American Cyanamide Company. It is described by the seller as having a surface area of 330 m²/g, 20 percent molybdenum and 1.5 percent potassium on a wide pore carbon. The catalyst comes as 1/16-inch (1.6 mm) extrudates having a bulk density of 0.63 g/cm³.

For Examples 1, 2 and 5, the following method which yields approximately 75 g of catalyst is used.

Using the incipient wetness technique, 50.0 g of carbon is impregnated with a solution consisting of 27.7 g of $(NH_4)_6Mo_7O_{24}\cdot4H_2O$ and 2.7 g of $K_2CO_3$ dissolved in a mixture of 10 cm³ of aqueous 30 percent $H_2O_2$ and 30 cm³ of water. The wet carbon is air-dried at room temperature and then calcined in a 2 percent $O_2$/98 percent $N_2$ atmosphere at 300° C. for 2 hours. The catalyst for Examples 1 and 2 is initially reduced in flowing $H_2$ at 500° C., 30 psig (0.31 MPa) and 450 hr$^{-1}$ for 16 hours. The catalyst for Example 5 is initially reduced in flowing $H_2$ at 500° C., 50 psig (0.45 MPa) and 200 hr$^{-1}$ for 4 hours. (Note: The preceding recipe is typical for a small batch of catalyst. Multiple catalyst batches are prepared and mixed for Example 5). In Examples 1, 2 and 5, the catalysts contain about 21 percent molybdenum and 1.5 percent potassium.

The following method which yields approximately 135 g of catalyst is used for Example 4.

Using the incipient wetness technique, 100 g of carbon is impregnated with a solution consisting of 12.21 g $(NH_4)_6Mo_7O_{24}\cdot4H_2O$ and 4.68 g of $K_2CO_3$ dissolved in a mixture of 4.55 cm³ of aqueous 30 percent $H_2O_2$ and 53.03 cm³ of distilled water. The wet carbon is dried in slowly moving air at 35° C. for 6–8 hours then calcined in flowing $N_2$ at 350° C. for 2–4 hours. The catalyst is loaded with 22.547 g of $Mo(CO)_6$ by dry mixing the solids at 80° C. in air for 1–2 hours and then is calcined at 350° C. in flowiing $N_2$ for 2–4 hours. The $Mo(CO)_6$ loading and calcination are repeated two additional times to give a total of 67.64 g of $Mo(CO)_6$ loaded. The catalyst is initially reduced in flowing $H_2$ at 500° C., 50 psig (0.45 MPa) and 215 hr$^{-1}$ for 4 hours. (Note: The preceding recipe is typical for a small batch of catalyst. Multiple catalyst batches are prepared and mixed for Example 4. In Example 4, catalysts average 22.5 percent molybdenum and 2.0 percent potassium.

The catalyst for Example 9 is alkalized MoS$_2$ on carbon.

A solution, heated to 50°-60° C., consisting of 11.9 g of (NH$_4$)$_6$Mo$_7$O$_{24}$.4H$_2$O, 2.5 g K$_2$CO$_3$, and 71.1 g of aqueous 22% (NH$_4$)$_2$S is added dropwise to 20 g 12-20 mesh MBV activated carbon (available from Witco Chemical Company) until the carbon is saturated. This takes about half of the solution. After air-drying at room temperature until the carbon no longer appears wet, the carbon is heated in flowing nitrogen at a temperature increasing by 2° C. per minute until 300° C. is reached. The 300° C. temperature is held for one hour. The next day the impregnated carbon is air dried at 150° C. for fifteen minutes, then re-impregnated with the remainder of the above solution. A small amount of aqueous 22% (NH$_4$)$_2$S is added to the solution before reheating it. After air drying the catalyst heating step in flowing nitrogen is repeated. The result shown in the Table is for a sample taken after several hundred hours of exposure of this catalyst to the reactants and reaction conditions.

The catalyst of Example 10 is unsupported or bulk alkalized molybdenum disulfide (MoS$_2$). It is made by thermally decomposing ammonium tetrathiomolybdate by heating in nitrogen at a temperature increasing by 5° C./minute until 580° C. is reached. This temperature is held for one hour. This mixture is ground together with sufficient potassium hydroxide to give 4 percent potassium in the final mixture. This catalyst has a surface area of about 27 m$^2$/g. The feed in this example includes 20 ppm hydrogen sulfide.

The catalyst of Example 11 is an alkalized molybdenum disulfide. Molybdenum trisulfide is prepared by treating a solution of 15 g (NH$_4$)$_6$Mo$_7$O$_{24}$.4H$_2$O dissolved in 106 cm$^3$ 22% aqueous (NH$_4$)$_2$S at 60° C. with 100 cm$^3$ concentrated acetic acid in 300 cm$^3$ water. The precipitate is dried and calcined at 500° C. for one hour in nitrogen to form molybdenum disulfide. This molybdenum disulfide is combined in a mortar in the following proportions: 66% MoS$_2$; 20% bentonite clay; 10% K$_2$CO$_3$; and 4% Sterotex ® lubricant. These ingredients are ground together and some is pelleted. Unpelleted material is used for the test. The feed for this example contains 50 ppm hydrogen sulfide.

The catalysts used in Examples 12-15 are prepared by obtaining experimental samples of molybdenum disulfide from Climax Molybdenum of Michigan, Ann Arbor, Mich. The designations are: 1619-6-2, at 129 m$^2$/g; 1619-8-2 at 95 m$^2$/g; 1619-12-2 at 82 m$^2$/g and 1619-13-2 at 85 m$^2$/g for Examples 12-15 respectively. Each of the molybdenum sulfides is combined in a mortar with bentonite clay; potassium carbonate and Sterotex ® pelleting lubricant to give catalysts containing 66% MoS$_2$; 20% clay; 10% potassium carbonate and 4% lubricant. After mixing together with a pestle these mixtures are pelleted and used to make alcohols. The feed in Examples 12-15 contains 50 ppm hydrogen sulfide.

The catalyst for Examples 16-18 is alkalized molybdenum disulfide made by thermally decomposing (NH$_4$)$_2$MoS$_4$. A solution of (NH$_4$)$_2$MoS$_4$ is prepared by mixing a solution of 180 g of (NH$_4$)$_4$Mo$_7$O$_{24}$.4H$_2$O in 400 cm$^3$ of water containing 100 cm$^3$ of concentrated ammonium hydroxide with 1300 cm$^3$ of 22% (NH$_4$)$_2$S solution. After stirring at 50°-60° C. for two hours, the (NH$_4$)$_2$MoS$_4$ solution is poured into a large shallow dish and evaporates to dryness overnight. The dry, dark-red (NH$_4$)$_2$MoS$_4$ is calcined for one hour at 500° C. in nitrogen. The resulting black molybdenum disulfide is combined to give 66% MoS$_2$; 10% potassium carbonate; 20% bentonite clay and 4% Sterotex ® pelleting lubricant. The catalyst is then pelleted to 3.2 mm diameter pellets. The feed in Example 16 contains 24 ppm hydrogen sulfide.

The catalyst for Example 19 is alkalized rhenium sulfide. Ten grams of Re$_2$O$_7$ is dissolved in 300 cm$^3$ of water, and then is neutralized with concentrated ammonium hydroxide to pH 9. Twenty five grams of Na$_2$S$_2$O$_3$.5H$_2$O is then dissolved in the basic Re$_2$O$_7$ solution. One hundred cubic centimeters of concentrated sulfuric acid is added to precipitate black (Re$_2$S$_7$) which is filtered, dried and calcined for one hour at 500° C. in nitrogen to give ReS$_2$. The Na$_2$S$_2$O$_3$.5H$_2$O supplies the alkali to the catalyst. For the test, 5.4 g of ReS$_2$ is mixed with 3 cm$^3$ of tabular alumina and loaded into the reactor and reduced in hydrogen containing 3% H$_2$S at 450° C. for 17 hours.

The catalyst for Example 20 is alkalized, coprecipitated, unsupported molybdenum/cobalt sulfide which has a Mo/Co atomic ratio of about 3:1. Fifteen grams of (NH$_4$)$_6$Mo$_7$O$_{24}$.4H$_2$O (0.085 moles of Mo) is dissolved in 106 cm$^3$ of 22% (NH$_4$)$_2$S in water and stirred at 60° C. for one hour to form (NH$_4$)$_2$MoOS$_4$. A solution of 7.1 g of Co(CH$_3$CO$_2$)$_2$.4H$_2$O (0.28 moles Co) in 200 cm$^3$ of water is prepared.

The two solutions are added simultaneously, dropwise to a stirred solution of concentrated acetic acid in a baffled flask at 50° C. over a one hour period. After stirring for one additional hour the reaction mix is filtered and the filter cake dried at room temperature and then calcined for one hour at 500° C. in an inert atmosphere such as nitrogen. A mortar and pestle are used to grind together 6.6 g of the calcined molybdenum/cobalt sulfide with 2.0 g bentonite clay, 1.0 g K$_2$CO$_3$ and 0.4 g Sterotex ® pelleting lubricant. This powder is used in unpelleted form, without pretreatment as the catalyst.

Preparation of Alcohols

Examples 1, 2, 9-15 and 19

In the general method used in these Examples, the reactor consists of a ½-inch (1.27 cm) stainless steel tube packed with catalyst. The total volume of catalyst is about 10 cubic centimeters. Premixed hydrogen, carbon monoxide, and nitrogen feed gases from a cylinder are compressed and regulated at the pressures stated. The feed gas mixture contains hydrogen and carbon monoxide at the ratios stated and about 5 percent by volume of nitrogen serving as an internal standard. Hydrogen sulfide is present in the feed streams as stated in the catalyst discussion. NoH$_2$S was added to the H$_2$CO feed for Examples 1, 2, 9 and 19.

The mixed feed gas passes through a bed of activated carbon at room temperature to remove iron and other carbonyls. The feed gas mixture then passes at the stated hourly space velocities through the fixed bed reactor which is maintained at the stated reaction temperatures by an electric furnace. The reactor products pass through a pressure letdown valve and flow past a gas chromatograph sampling point into a dry ice cooled condenser. Liquid products from the condenser are collected, sampled and analyzed.

Examples 3, 6–8 and 16–18

In the method used in these Examples, the reactor is a ½-inch (1.27 cm) stainless steel tube packed with catalyst. The total volume of catalyst is about 40 cubic centimeters. Premixed carbon monoxide and nitrogen from a cylinder pass through a molecular sieve bed at ambient temperature to remove iron and other carbonyls. Hydrogen from a cylinder is then mixed with the carbon monoxide and nitrogen and the mixture is compressed to the pressures stated. The feed gas mixture contains hydrogen and carbon monoxide at the ratios stated and about 5 percent by volume of nitrogen serving as an internal standard. The feed to Examples 16–18 contains 50 ppm $H_2S$. $H_2S$ is not added to the $H_2$/CO feed for Examples 3, 6 and 8.

The feed gas mixture is preheated and then passes at the stated hourly space velocities through the fixed bed reactor which is maintained at the stated reaction temperatures by an electric furnace. The reactor products pass into a vapor/liquid separator at room temperature. The product gases leaving the separator flow past a gas chromatograph sampling point, through a pressure letdown valve into a dry ice cooled condenser. Liquid products are collected, sampled and analyzed.

Example 4

In Example 4, the reactor consists of a jacketed stainless steel pipe packed with catalyst. The total volume of catalyst is about one cubic foot (0.028 m³). The reactor jacket carries a heat-transfer fluid to remove the heat of reaction. The carbon monoxide feed gas passes through a bed of activated carbon at room temperature to remove iron and other carbonyls. The hydrogen and carbon monoxide feed gases are then mixed at the ratio stated. Five percent by volume of nitrogen is added to the feed gas as an internal standard and the mixture is compressed to the pressure stated. The feed gas mixture is preheated to the stated reaction temperature and then passed through the fixed bed reactor at the stated hourly space velocity. The reactor products pass through a water-cooled condenser into a high pressure vapor/liquid separator. The product liquids from the high pressure separator pass through a pressure letdown valve into a low pressure vapor/liquid separator. The product gases leaving the high pressure separator pass through a pressure letdown valve, are combined with the gases from the low pressure separator, and flow past a gas chromatograph sampling point. Liquid products from the low pressure separator are collected in a receiver where they may be sampled and analyzed.

Example 5

In Example 5, the reactor consists of a jacketed stainless steel pipe with internal tubes and a fluidized bed catalyst. The total volume of catalyst is about 0.65 cubic foot (0.018 m³). The reactor jacket and internal tubes carry a heat transfer fluid to remove the heat of reaction. The feed gas and product recovery systems described in Example 4 are used for the fluidized bed reactor. The reactants serve as the fluidizing medium.

Example 20

In Example 20, the reactor consists of a one-half inch (1.27 cm) stainless steel tube packed with catalyst. The total volume of catalyst is about 6 cm³. Premixed hydrogen, carbon monoxide, and nitrogen feed gases from cylinders are compressed and regulated at the pressures stated in the table. The feed gas mixture contains hydrogen and carbon monoxide at the stated molar ratios and about five percent by volume of nitrogen serving as an internal standard. About 50 ppm of $H_2S$ is also present in the feed gas.

The mixed feed gas passes through the bed of activated carbon at room temperature to remove iron and other carbonyl contaminants. The feed gas then passes at the stated hourly space velocity through the fixed bed reactor which is maintained at the stated reaction temperature by an electric air recirculated oven. The reactor effluent passes through a gas liquid separator at ambient temperature and at the reaction pressure stated, in series with a dry ice trap at ambient pressure. Both gas and liquid phases are analyzed to give the results in the Table.

TABLE

| | Example | | | | | | | | | |
|---|---|---|---|---|---|---|---|---|---|---|
| | 1 | 2 | 3 | 4 | 5 | 6 | 7 | 8 | 9 | 10 |
| Temp. (°C.) | 262 | 235 | 300 | 318 | 297 | 301 | 300 | 300 | 260 | 262 |
| Pressure (psig) | 1063 | 1230 | 1500 | 1500 | 1010 | 2000 | 2500 | 2500 | 1200 | 1175 |
| (MPa) | (7.43) | (8.58) | (10.45) | (10.45) | (7.07) | (13.89) | (17.34) | (17.34) | (8.38) | (8.20) |
| $H_2$/CO (molar ratio) | 0.84 | 0.82 | 1.21 | 1.50 | 0.82 | 1.21 | 1.21 | 1.21 | 1.02 | 0.76 |
| GHSV (hr$^{-1}$) | 372 | 220 | 1950 | 1121 | 1747 | 1950 | 1950 | 1500 | 1283 | 676 |
| Recycle ratio | 0 | 0 | 0 | 0 | 0 | 0 | 0 | 0 | 0 | 0 |
| CO Conversion (%) | 23.4 | 31.8 | 20.2 | 41.4 | 26.8 | 25.5 | 31.0 | 27.8 | 14.7 | 16.5 |
| Wt. Units CO converted per wt. unit of catalyst per hr | 0.097 | 0.079 | 0.324 | 0.324 | 0.523 | 0.410 | 0.498 | 0.343 | 0.177 | 0.121 |
| $CO_2$ produced[1] (%) | 40.2 | 36.9 | 36.9 | 38.5 | 45.0 | 37.6 | 37.3 | 37.3 | 22.1 | 28.0 |
| Selectivities[2] (%) | | | | | | | | | | |
| Gas Phase | | | | | | | | | | |
| $CH_4$ | 26.0 | 19.2 | 17.5 | 29.8 | 36.6 | 16.8 | 15.8 | 15.9 | 10.9 | 10.6 |
| $C_2+$ hydrocarbons | 17.2 | 13.4 | 15.1 | 18.5 | 34.0 | 14.2 | 13.5 | 14.6 | 3.5 | 2.7 |
| Subtotal | 43.2 | 32.6 | 32.6 | 48.3 | 70.6 | 31.0 | 29.3 | 30.5 | 14.4 | 13.3 |
| Liquid Phase | | | | | | | | | | |
| Methanol | 25.0 | 22.9 | 25.6 | 28.3 | 12.2 | 23.4 | 26.0 | 21.3 | 56.3 | 42.5 |
| Ethanol | 12.4 | 14.1 | 17.3 | 12.5 | 8.3 | 15.5 | 17.4 | 16.2 | 22.8 | 32.7 |
| Propanols | 6.8 | 8.9 | 10.1 | 5.4 | 3.6 | 8.3 | 8.9 | 9.1 | 5.3 | 7.5 |
| Butanols | 2.0 | 2.9 | 2.7 | 1.1 | — | 3.0 | 3.1 | 3.4 | 1.1 | 1.4 |
| Pentanols | 0.3 | 1.6 | 0.6 | — | — | 0.6 | 1.1 | 1.3 | 0.03 | 0.1 |
| Subtotal | 46.5 | 50.4 | 56.3 | 47.3 | 24.1 | 50.8 | 56.5 | 51.3 | 85.53 | 84.2 |
| Other oxygenates[3] and hydrocarbons | 10.3 | 17.0 | 11.1 | 4.4 | 5.3 | 18.2 | 14.2 | 18.2 | 0.07 | 2.5 |

TABLE-continued

| H$_2$O[4] (wt. %) | 2.9 | 1.9 | 3.8 | 5.8 | 5.9 | 3.4 | 3.7 | 3.6 | 1.2 | 0.8 |
|---|---|---|---|---|---|---|---|---|---|---|

| | Example | | | | | | | | | |
|---|---|---|---|---|---|---|---|---|---|---|
| | 11 | 12 | 13 | 14 | 15 | 16 | 17 | 18 | 19 | 20 |
| Temp. (°C.) | 255 | 255 | 258 | 250 | 250 | 260 | 265 | 284 | 284 | 295 |
| Pressure (psig) | 1500 | 1350 | 1350 | 1350 | 1350 | 2000 | 3050 | 3050 | 1350 | 1500 |
| (MPa) | (10.44) | (9.41) | (9.41) | (9.41) | (9.41) | (13.89) | (21.13) | (21.13) | (9.41) | (10.44) |
| H$_2$/CO (molar ratio) | 1.02 | 1.0 | 1.0 | 1.0 | 1.0 | 1.1 | 1.2 | 1.2 | 0.9 | 0.98 |
| GHSV (hr$^{-1}$) | 3171 | 2254 | 3140 | 2300 | 1934 | 3150 | 3900 | 5220 | — | 1050 |
| Recycle ratio | 0 | 0 | 0 | 0 | 0 | 0 | 0 | 0 | 0 | 0 |
| CO Conversion (%) | 16.3 | 13.3 | 14.6 | 15.5 | 14.0 | 10.2 | 14.5 | 26.1 | 6.8 | 29.2 |
| Wt. Units CO converted per wt. unit of catalyst per hr | 0.26 | 0.15 | 0.24 | 0.18 | 0.14 | 0.158 | 0.271 | 0.659 | .09 | 0.13 |
| CO$_2$ produced[1] (%) | 24.5 | 25.6 | 26.2 | 26.0 | 27.8 | 27.0 | 24.7 | 28.3 | 36.8 | 31.3 |
| Selectivities[2] (%) | | | | | | | | | | |
| Gas Phase | | | | | | | | | | |
| CH$_4$ | 12.6 | 10.8 | 15.2 | 14.1 | 15.0 | 14.4 | 11.2 | 17.8 | 48.8 | 11.3 |
| C$_2$+ hydrocarbons | 2.2 | 1.6 | 2.5 | 2.8 | 3.3 | 0.0 | 0.5 | 2.6 | 5.7 | 3.2 |
| Subtotal | 14.8 | 12.4 | 17.7 | 16.9 | 18.3 | 14.4 | 11.7 | 20.4 | 54.5 | 14.5 |
| Liquid Phase | | | | | | | | | | |
| Methanol | 33.8 | 35.2 | 33.0 | 30.5 | 30.6 | 49.0 | 48.1 | 43.3 | 33.1 | 22.7 |
| Ethanol | 24.9 | 26.6 | 25.7 | 24.6 | 27.0 | 25.2 | 25.8 | 23.2 | 10.3 | 40.7 |
| Propanols | 5.6 | 7.0 | 5.8 | 5.8 | 5.8 | 6.9 | 7.8 | 7.1 | 1.2 | 12.7 |
| Butanols | 1.6 | 2.0 | 1.9 | 2.0 | 1.6 | 1.6 | 2.7 | 2.4 | 0.2 | 3.5 |
| Pentanols | 0.1 | 0.3 | 0.5 | 0.5 | 0.3 | — | — | — | 0 | 1.2 |
| Subtotal | 65.8 | 71.1 | 66.9 | 63.4 | 65.3 | 82.7 | 84.4 | 76.0 | 44.8 | 80.8 |
| Other oxygenates[3] and hydrocarbons | 19.4 | 16.5 | 15.4 | 19.7 | 16.4 | 2.9 | 3.9 | 3.6 | 0.7 | 4.7 |
| H$_2$O[4] (wt. %) | 1.9 | 1.4 | 1.5 | 1.6 | 1.7 | 0.78 | 1.55 | 1.55 | 10.0 | 2.3 |

[1]100 × moles of CO$_2$ formed for each mole of CO converted in the reactor.
[2]Selectivities, except for CO$_2$, are based on carbon mole selectivity on a CO$_2$ free basis.
[3]Assumed a carbon number of 4 for other oxygenates.
[4]Water is calculated as weight percent of the liquid phase.

Although the invention has been described in considerable detail, it must be understood that such detail is for the purpose of illustration only and that many variations and modifications can be made by one skilled in the art without departing from the spirit and scope of the invention.

We claim:

1. A process for producing alcohols comprising contacting a mixture of hydrogen and carbon monoxide with a catalyst comprising:
   (1) at least one element selected from the group consisting of molybdenum and tungsten in free or combined form;
   (2) a promoter containing an alkali or an alkaline earth element or a mixture thereof in free or combined form;
said catalyst excluding rhodium or ruthenium and containing less than 2 weight percent copper based on the weight of carbon oxide hydrogenation active metals; under conditions, including a pressure of at least about 500 psig, sufficient to form an alcohol fraction boiling in the range of motor gasoline and containing less than about 5 weight percent C$_5$+ alcohols in at least about 20 percent CO$_2$ free carbon selectivity.

2. The process of claim 1 conducted at a pressure of at least about 750 psig.

3. The process of claim 2 conducted at a pressure of at least about 1,000 psig.

4. The process of claim 3 conducted at a pressure of from about 1,500 psig to about 4,000 psig.

5. The process of claim 1 conducted at a temperature of from about 200° C. to about 350° C.

6. The process of claim 3 conducted at a temperature of from about 240° C. to about 325° C.

7. The process of claim 1 wherein the H$_2$/CO gas hourly space velocity is from about 300 to about 5,000 hr$^{-1}$.

8. The process of claim 1 wherein at least a portion of unconverted hydrogen and/or carbon monoxide feed is recycled to the reaction.

9. The process of claim 3 wherein the molar ratio of recycled feed to fresh feed is at least about three.

10. The process of claim 3 wherein the alcohol fraction and any hydrocarbons formed are substantially removed from the recycled feed prior to recycling.

11. The process of claim 5 wherein the alcohol fraction contains from about 20 to about 70 weight percent of methanol.

12. The process of claim 11 wherein the alcohol fraction contains at least about 15 weight percent ethanol.

13. The process of claim 1 wherein the distillation endpoint of the alcohol fraction is equal to or less than about 225° C.

14. The process of claim 1 wherein an alcohol fraction containing C$_1$-C$_8$ alcohols in at least 20 percent CO$_2$ free carbon selectivity is formed.

15. The process of claim 12 wherein an alcohol fraction containing C$_1$-C$_4$ alcohols in at least about 20 percent CO$_2$ free carbon selectivity is formed.

16. The process of claim 15 wherein an alcohol fraction containing C$_1$-C$_4$ alcohols in at least about 30 percent CO$_2$ free carbon selectivity is formed.

17. The process of claim 16 wherein an alcohol fraction containing C$_1$-C$_4$ alcohols in at least about 50 percent CO$_2$ free carbon selectivity is formed.

18. The process of claim 17 wherein an alcohol fraction containing C$_1$-C$_4$ alcohols in at least about 70 percent CO$_2$ free carbon selectivity is formed.

19. The process of claim 17 wherein the alcohol fraction is produced at a rate of about 0.1 weight units or more of alcohol fraction per weight unit of catalyst per hour.

20. The process of claim 19 wherein the alcohol fraction is produced at a rate of about 0.2 weight units or more of alcohol fraction per weight unit of catalyst per hour.

21. The process of claim 17 wherein the promoter consists essentially of an alkali element in free or combined form.

22. The process of claim 21 wherein the promoter consists essentially of sodium or potassium in free or combined form.

23. The process of claim 22 wherein the promoter consists essentially of potassium in free or combined form.

24. The process of claim 21 wherein the promoter is present at a level sufficient to render the catalyst neutral or basic.

25. The process of claim 21 wherein the promoter is present at a level of at least about 0.5 percent by weight as free element in the total catalyst.

26. The process of claim 25 wherein the promoter is present at a level of at from about 0.5 to about 20 percent by weight as free element in the total catalyst.

27. The process of claim 21 wherein the catalyst contains molybdenum.

28. The process of claim 27 wherein the molybdenum is present as a carbonyl, sulfide, carbide or oxide of the element, as the free element or as a mixture of these.

29. The process of claim 28 wherein the molybdenum is present as a sulfide.

30. The process of claim 29 wherein the molybdenum is present at a level of at least about 5 percent by weight of the total catalyst.

31. The process of claim 30 wherein the molybdenum is present at a level of from about 5 percent to about 70 percent by weight of the total catalyst.

32. The process of claim 30 wherein the catalyst contains less than 25 weight percent of carbon monoxide hydrogenation active metals other than molybdenum.

33. The process of claim 32 wherein the catalyst contains less than 2 weight percent of carbon monoxide hydrogenation active metals other than the molybdenum.

34. The process of claim 30 wherein the catalyst excludes iron, copper or zinc.

35. The process of claim 34 wherein the catalyst excludes halogen, titanium, vanadium, cerium, thorium, uranium, iridium, palladium, platinum, silver or cadmium.

36. The process of claim 1 wherein the catalyst excludes copper.

37. A process for producing alcohols comprising contacting a mixture of hydrogen and carbon monoxide with a catalyst consisting essentially of:
   (1) at least one element selected from the group consisting of molybdenum and tungsten in free or combined form;
   (2) a promoter containing an alkali or an alkaline earth element or a mixture thereof in free or combined form;
under conditions, including a pressure of at least about 500 psig, sufficient to form an alcohol fraction boiling in the range of motor gasoline and containing less than about 5 weight percent $C_{5}+$ alcohols in at least about 20 percent $CO_2$ free carbon selectivity.

38. The process of claim 37 wherein the catalyst contains molybdenum.

39. The process of claim 38 wherein the catalyst contains molybdenum sulfide.

40. A process for producing alcohols comprising contacting a mixture of hydrogen and carbon monoxide with a catalyst comprising:
   (1) at least one element selected from the group consisting of molybdenum and tungsten in sulfide form;
   (2) a promoter containing an alkali or an alkaline earth element or a mixture thereof in free or combined form;
under conditions, including a pressure of at least about 500 psig, sufficient to form an alcohol fraction boiling in the range of motor gasoline and containing less than about 5 weight percent $C_{5}+$ alcohols in at least about 20 percent $CO_2$ free carbon selectivity.

41. The process of claim 40 wherein the catalyst contains molybdenum.

* * * * *

UNITED STATES PATENT AND TRADEMARK OFFICE
CERTIFICATE OF CORRECTION

PATENT NO. : 4,749,724
DATED : June 7, 1988
INVENTOR(S) : George J. Quarderer, et al It is certified that error appears in the above-identified patent and that said Letters Patent is hereby corrected as shown below:

Col. 4, line 22, "alcohol products" should read --alcohol product--.

Col. 6, line 41, "magnesium" should read --magnesium,--.

Col. 10, line 65, "flowiing" should read --flowing--.

Col. 15, line 3, in the Table, the subtitle "Example" should be placed as a subtitle, on the same line, at the left flush margin.

Col.16, line 39, claim 9, "The process of claim 3" should read --The process of claim 8--.

Col.16, line 41, claim 10, "The process of claim 3" should read --The process of claim 8--.

Signed and Sealed this

Eighteenth Day of May, 1993

Attest:

MICHAEL K. KIRK

*Attesting Officer*      Acting Commissioner of Patents and Trademarks